United States Patent
Roubin et al.

[11] Patent Number: 5,827,321
[45] Date of Patent: Oct. 27, 1998

[54] NON-FORESHORTENING INTRALUMINAL PROSTHESIS

[75] Inventors: Gary S. Roubin, Birmingham, Ala.; Geoffrey Hamilton White, Sydney, Australia; Sriram S. Iyer, Birmingham, Ala.; Russell J. Redmond, Goleta; Claude A. Vidal, Santa Barbara, both of Calif.

[73] Assignee: Cornerstone Devices, Inc., San Clemente, Calif.

[21] Appl. No.: 797,814

[22] Filed: Feb. 7, 1997

[51] Int. Cl.⁶ .................................................. A61M 29/00
[52] U.S. Cl. .............................. 606/195; 606/198; 623/1; 623/12
[58] Field of Search ..................... 606/191, 194, 606/195, 198; 623/1, 12

[56] References Cited

U.S. PATENT DOCUMENTS

| | | |
|---|---|---|
| 3,868,956 | 3/1975 | Alfidi et al. . |
| 4,512,338 | 4/1985 | Balko et al. . |
| 4,580,568 | 4/1986 | Gianturco . |
| 4,649,922 | 3/1987 | Wiktor . |
| 4,655,771 | 4/1987 | Wallsten ................................. 623/1 |
| 4,681,110 | 7/1987 | Wiktor . |
| 4,732,152 | 3/1988 | Wallsten et al. . |
| 4,733,665 | 3/1988 | Palmaz . |
| 4,795,458 | 1/1989 | Regan . |
| 4,830,003 | 5/1989 | Wolff et al. . |
| 4,878,906 | 11/1989 | Lindemann et al. ................... 623/1 |
| 4,886,062 | 12/1989 | Wiktor . |
| 4,913,141 | 4/1990 | Hillstead . |
| 5,064,435 | 11/1991 | Porter . |
| 5,147,370 | 9/1992 | McNamara et al. .................. 606/108 |
| 5,192,297 | 3/1993 | Hull ..................................... 606/195 |
| 5,201,757 | 4/1993 | Heyn et al. .......................... 606/198 |
| 5,234,457 | 8/1993 | Andersen ............................. 606/198 |
| 5,282,824 | 2/1994 | Gianturco ............................ 606/198 |
| 5,330,500 | 7/1994 | Song ................................... 606/198 |
| 5,354,309 | 10/1994 | Schnepp-Pesch et al. ........... 606/198 |
| 5,405,377 | 4/1995 | Cragg ..................................... 623/1 |
| 5,415,664 | 5/1995 | Pinchuk ............................... 606/108 |
| 5,441,515 | 8/1995 | Khosravi et al. .................... 606/194 |
| 5,445,646 | 8/1995 | Euteneuer et al. ................... 606/198 |
| 5,449,373 | 9/1995 | Pinchasik et al. ................... 606/198 |
| 5,476,508 | 12/1995 | Amstrup .................................. 623/1 |
| 5,507,767 | 4/1996 | Maeda et al. ........................ 606/198 |
| 5,507,771 | 4/1996 | Gianturco ............................ 606/198 |
| 5,545,211 | 8/1996 | An et al. ................................ 623/1 |
| 5,562,697 | 10/1996 | Christiansen ........................ 606/191 |
| 5,562,725 | 10/1996 | Schmitt et al. ......................... 623/1 |
| 5,591,195 | 1/1997 | Tahen et al. ......................... 606/194 |

FOREIGN PATENT DOCUMENTS

| | | |
|---|---|---|
| 382014 | 8/1990 | European Pat. Off. . |
| WO9421196 | 9/1994 | WIPO . |

*Primary Examiner*—Michael Powell Buiz
*Assistant Examiner*—David O. Reip
*Attorney, Agent, or Firm*—Raymond Sun

[57] ABSTRACT

An intraluminal prosthesis is provided with a plurality of annular elements. Each annular element includes a plurality of struts and apices connected to form an annular configuration. Each annular element has a compressed state and an expanded state, and has a longitudinal dimension which is smaller in the expanded state than in the compressed state. A plurality of connecting members connect the apices of adjacent annular elements. The connecting members have a plurality of alternating segments that function to compensate for the smaller longitudinal dimension of each annular element in the expanded state. The stent may be provided with varying flexibility along its length and/or circumference, and may include segments that have different diameters.

54 Claims, 6 Drawing Sheets

EXPANDED
$l_1 = h \cos \theta_1$
$\Delta l = h(\cos \theta_2 - \theta_1)$

COMPRESSED
$l_2 = h \cos \theta_2$
$\Delta l = h(\cos \theta_2 - \theta_1)$

EXPANDED
$\ell_2 - \ell_1 = L_1 - L_2$

COMPRESSED
$\ell_2 - \ell_1 = L_1 - L_2$

EXPANDED

COMPRESSED

NON-FORESHORTENING INTRALUMINAL PROSTHESIS

BACKGROUND OF THE INVENTION

1. Field of the Invention

The present invention relates to an intraluminal prosthesis for implantation into a mammalian vessel, and in particular, to an intraluminal stent that is delivered in a compressed state to a specific location inside the lumen of a mammalian vessel and then deployed to an expanded state to support the vessel. The intraluminal stent is provided with a structural configuration that maintains the prosthesis at substantially the same length in both the compressed and expanded states. The intraluminal stent may also be provided with varying rigidity or flexibility along its length.

2. Description of the Prior Art

Intraluminal prosthesis, such as stents, are commonly used in the repair of aneurysms, as liners for vessels, or to provide mechanical support to prevent the collapse of stenosed or occluded vessels. These stents are typically delivered in a compressed state to a specific location inside the lumen of a vessel or other tubular structures, and then deployed at that location of the lumen to an expanded state. The stent has a diameter in its expanded state which is several times larger than the diameter of the stent in its compressed state. These stents are also frequently deployed in the treatment of atherosclerotic stenosis in blood vessels, especially after percutaneous transluminal coronary angioplasty (PTCA) procedures, to improve the results of the procedure and to reduce the likelihood of restenosis.

The positioning of a stent at the desired location in the lumen of a body vessel is a critical factor that affects the performance of the stent and the success of the medical procedure. Since the region in a lumen at which the stent is to be deployed is usually very difficult for a physician to access, it is essential that the stent's deployed diameter and length be known before the physician can accurately position a stent with the correct size at the precise location. For example, since the diameter and the length of the diseased or damaged segment or region of the body vessel can vary for different body vessels, disease states, and deployment purposes, it is important that a stent having the precise diameter and length be delivered to this region for deployment.

Careful sizing of this region of the lumen of the body vessel may pose a difficult challenge for many physicians who know the exact dimensions of the body vessel at this region, but are not certain about the stent's deployed diameter and length. This is due to a foreshortening effect which is experienced by many stents when they are expanded from their compressed state to their expanded state.

This foreshortening effect is illustrated in FIGS. 1A, 1B, 2A and 2B, which illustrate portions 20 of a stent having a mesh-like pattern made up of V-shaped struts or legs 22 and 24 connected at their apices 26. Two pairs of these V-shaped struts 22, 24 are illustrated in this portion 20 of the stent. Each of these struts 22 and 24 has a length h. FIG. 1B illustrates the portion 20 of the stent in a fully compressed state, in which the length h has a longitudinal or horizontal component $l_2$ (see FIG. 2B), and FIG. 1A illustrates the same portion 20 of the stent in a fully expanded state, in which the length h has a longitudinal or horizontal component $l_1$ (see FIG. 2A). As illustrated by the imaginary lines 28 and 30 in FIGS. 1A and 1B, and in FIGS. 2A and 2B, $l_1$ is shorter than $l_2$ because the angle which the strut 22 assumes with respect to the horizontal axis is greater when in the expanded state, so the length of the expanded portion 20 is shorter than the length of the compressed portion 20 by a length of 2d. This foreshortening is caused by the shortening of the longitudinal component 1 of the struts 22 and 24 as the stent is expanded from the compressed state to the expanded state.

This foreshortening effect is troublesome because it is not easy to determine the exact dimension of this foreshortened length 2d. The physician must make this calculation based on the material of the stent, the body vessel being treated, and the expected diameter of the stent when properly deployed in the lumen of the body vessel. For example, the foreshortened length 2d will vary when the same stent is deployed in vessels having different diameters at the region of deployment.

In addition, there are certain body vessels that experience a change in vessel lumen diameter, anatomy or disease state along their lengths. Stents to be deployed at such vessels will need to be capable of addressing or adapting to these changes.

An example of such a body vessel are the carotid arteries. Blood is delivered from the heart to the head via the common carotid arteries. These arteries are approximately 8–10 mm in lumen diameter as they make their way along the neck up to a position just below and behind the ear. At this point, the common carotid artery branches into a 6–8 mm lumen diameter internal carotid artery, which feeds blood to the brain, and a 6–8 mm lumen diameter external carotid artery, which supplies blood to the face and scalp. Atherosclerotic lesions of the carotid artery tend to occur around this bifurcation of the common carotid artery into the internal and external carotid arteries, so stents often need to be deployed at this bifurcation.

Another example are the iliac arteries, which have a lumen diameter of about 8–10 mm at the common iliac artery but which decrease to a lumen diameter of about 6–7 mm at the external iliac artery. The common iliac arteries experience more localized stenosis or occlusive lesion which are quite often calcific and usually require a shorter stent with greater radial strength or rigidity. More diffused atherosclerotic disease of the iliac system will commonly involve both the common and external iliac arteries, and necessitate a longer stent having increased flexibility that is suitable for deployment in the tortuous angulation experienced by the iliac system.

The femoropopliteal system similarly experiences localized and diffused stenotic lesions. In addition, the flexibility of a stent is important where deployed at locations of vessels that are affected by movements of joints, such as the hip joint or the knee joint.

The renal arteries provide yet another useful example. The initial 1 cm or so at the orifice of a renal artery is often quite firmly narrowed due to atheroma and calcification, and is relatively straight, while the remainder of the length of the renal artery is relatively curved. As a result, a stent intended for implantation at the renal arteries should be relatively rigid for its first 1.5 cm or so, and then become more flexible and compliant.

Thus, there remains a need for an intraluminal prosthesis that maintains a consistent length in both its fully compressed and fully expanded states, and in all states between its fully compressed and fully expanded states. There also remains a need for a stent which can accomodate body vessels having varying lumen diameters, different anatomies, and different disease states.

SUMMARY OF THE DISCLOSURE

In order to accomplish the objects of the present invention, there is provided a stent having a plurality of annular elements. Each annular element has a compressed state and an expanded state, and has a longitudinal dimension which is smaller in the expanded state than in the compressed state. A plurality of connecting members connect adjacent annular elements, with the connecting members operating to compensate for the smaller longitudinal dimension of each annular element in the expanded state.

In one embodiment of the present invention, each annular element includes a plurality of struts and apices connected to form an annular configuration. The connecting members are connected to the apices of the adjacent annular elements. The plurality of struts of the annular elements include left and right struts, with each pair of left and right struts connected to each other at an apex. Each strut has a longitudinal dimension which is smaller when the annular element is in the expanded state than in the compressed state.

In one embodiment of the present invention, at least one of the annular elements may have a closed configuration such that the plurality of alternating struts and apices are connected to each other to form a closed annular element. In addition, it is also possible for at least one of the annular elements to assume an open configuration such that the plurality of alternating struts and apices are not connected at at least one location.

In a preferred embodiment of the present invention, the connecting members have a plurality of alternating segments. In one embodiment, the connecting members have a plurality of alternating curved segments defining alternating top and bottom curved apices. In another embodiment, the connecting members have a plurality of alternating curved and straight segments. In a further embodiment, the connecting members have a plurality of alternating and angled straight segments. The connecting members have a larger longitudinal dimension when each annular element is in the expanded state than in the compressed state to compensate for the smaller longitudinal dimension of the annular element in the expanded state.

The stent according to the present invention further includes a plurality of apertures defined by adjacent annular elements and connecting members. In one embodiment, it is possible for the apertures of different segments of the stent to have different sizes.

The stent according to the present invention further provides a plurality of segments, at least two of which have a different degree of flexibility. In one embodiment, the varying flexibility is accomplished by forming a plurality of gaps. These gaps may be formed by omitting one or more of the connecting members, or portions of connecting members, between adjacent annular elements, or by omitting one or more of the struts, or by omitting connecting members and struts. In another embodiment, the varying flexibility is accomplished by providing the apertures of different stent segments with different sizes.

The stent according to the present invention may further provide segments that assume different diameters when the stent is in its expanded state. The differing diameters may be accomplished by providing the stent in a tapered or a stepped configuration.

In a preferred embodiment according to the present invention, the stent is made from a shape memory alloy, such as Nitinol, although other materials such as stainless steel, tantalum, titanium, elgiloy, gold, platinum, or any other metal or alloy, or polymers or composites, having sufficient biocompatibility, rigidity, flexibility, radial strength, radiopacity and antithrombogenicity can be used for the stent material.

Thus, the stent according to the present invention maintains a consistent length in both its fully compressed and fully expanded states, and in all states between its fully compressed and fully expanded states. As a result, the stent according to the present invention facilitates accurate sizing and deployment, thereby simplifying, and possibly reducing the time needed for, the medical procedure. In addition, the stent according to the present invention provides varying flexibility and rigidity along its length and/or circumference, as well as varying diameters along different segments of the stent, thereby facilitating the treatment of body vessels having varying lumen diameters, different anatomies and different disease states.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The intraluminal prosthesis according to the present invention is a stent, although the principles of the present invention are also applicable to other prosthesis such as liners and filters. The stent is delivered to a desired location in the lumen of a body vessel in a compressed state, and is then deployed by expanding it to its expanded state. The stent maintains substantially the same length in both its fully compressed and fully expanded states, and in all states between these two states. The stent may be provided with varying flexibility or rigidity along different segments thereof to allow the stent to be deployed in body vessels having different anatomies and different disease states. The stent may also be provided in a configuration in which the same stent has varying diameters along different portions of the stent to facilitate implantation in body vessels that have varying diameters.

The stent according to the present invention can be a self-expanding stent, or a stent that is radially expandable by inflating a balloon or expanded by an expansion member, or a stent that is expanded by the use of radio frequency which provides heat to cause the stent to change its size. The stent may also be coated with coverings of PTFE, dacron, or other biocompatible materials to form a combined stent-graft prosthesis. The vessels in which the stent of the present invention can be deployed include but are not limited to natural body vessels such as ducts, arteries, trachea, veins, ureters and the esophagus, and artificial vessels such as grafts.

1. A Preferred Embodiment

Figure 1A:
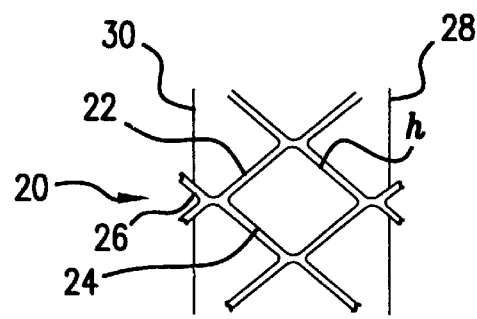
FIG. 1A is a side elevational view of a portion of a prior art stent in its expanded state.
Figure 1B:
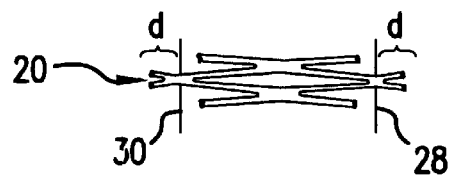
FIG. 1B is a side elevational view of the portion of FIG. 1A in its compressed state.
Figure 2A:
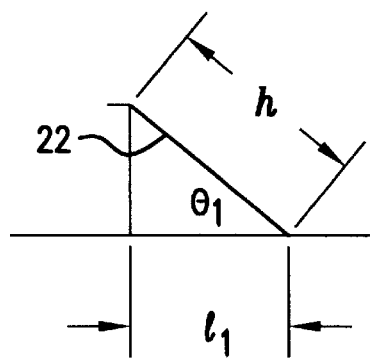
FIG. 2A illustrates the longitudinal component of a strut of the stent of FIGS. 1A and 1B when the stent is in its expanded state.
Figure 2B:
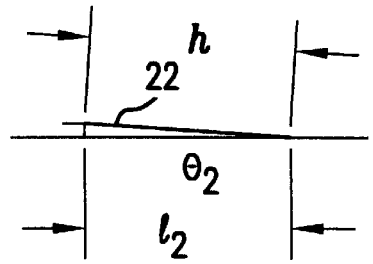
FIG. 2B illustrates the longitudinal component of a strut of the stent of FIGS. 1A and 1B when the stent is in its compressed state.
Figure 3:
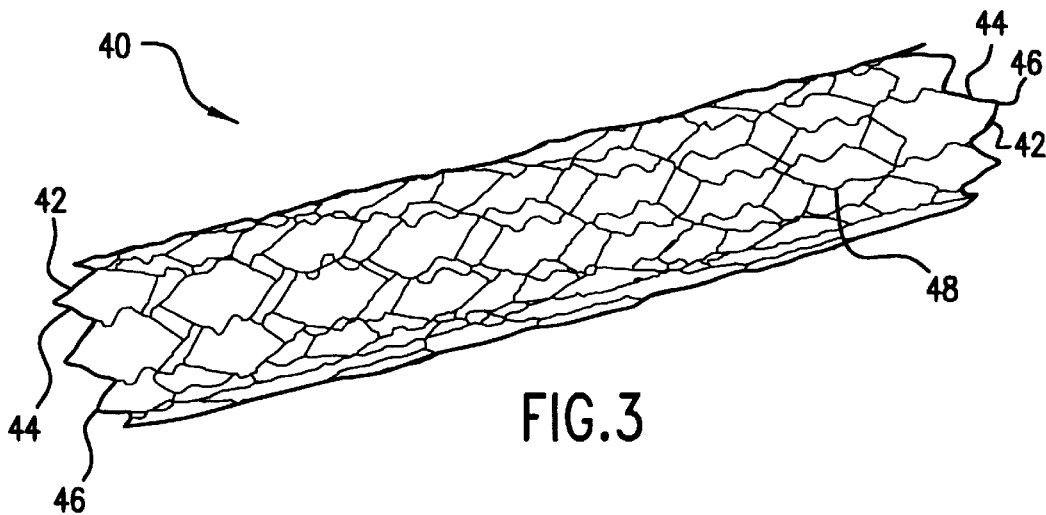
FIG. 3 is a perspective view of a stent according to the present invention.

A stent 40 according to the present invention is illustrated in FIGS. 3–6 in its expanded state. Referring to FIG. 3, the stent 40 has a tubular configuration and is made up of a plurality of pairs of substantially V-shaped struts connected at their apices, and by connecting a plurality of connecting members to the apices of each pair of V-shaped struts. FIGS. 4A and 4B illustrate a portion of the stent 40 in greater detail. The stent 40 has a plurality of pairs of alternating left struts 42 and right struts 44. Each pair of left and right struts 42, 44 is connected at an apex 46 to form a substantially V-shape for the pair. The left strut 42 is defined as being to the left of each apex 46, and the right strut 44 is defined as being to the right of each apex 46. The left struts 42 and right struts 44 are alternating since the left strut 42 of one pair of V-shaped struts is also the left strut of the adjacent pair of V-shaped struts, and the right strut 44 of one pair of V-shaped struts is also the right strut of the adjacent pair of V-shaped struts. In this manner, the alternating left and right struts 42 and 44 extend in an annular manner around the tubular stent 40 to form an annular element. Each apex 46 is connected to another apex 46 by a connecting member 48. Therefore, the stent 40 resembles a tubular lattice formed by pairs of V-shaped struts 42, 44 connected to themselves and having their apices 46 connected by the connecting members 48. As shown in FIG. 3, both ends of the stent 40 are defined by a plurality of alternating left and right struts 42, 44, with the extremity of both ends defined by the apices 46 of these alternating left and right struts 42, 44.

Figure 4A:
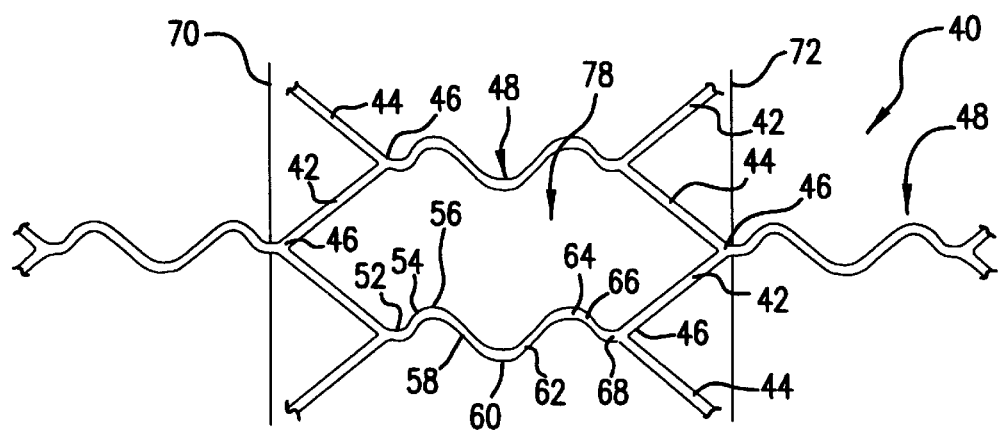
FIG. 4A is a side elevational view of a portion of the stent of FIG. 3 in its expanded state.
Figure 4B:
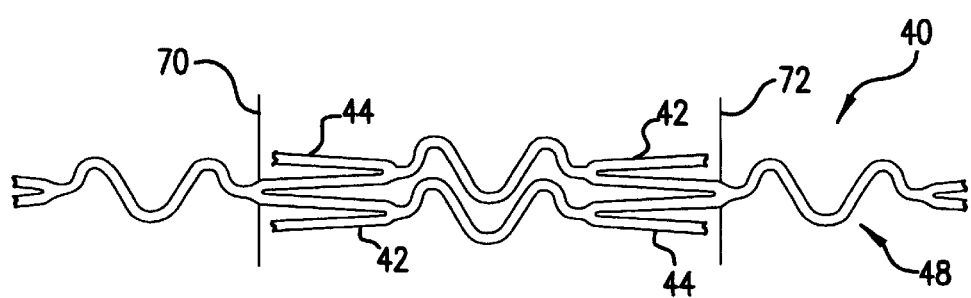
FIG. 4B is a side elevational view of the portion of FIG. 4A in its compressed state.
Figure 5A:
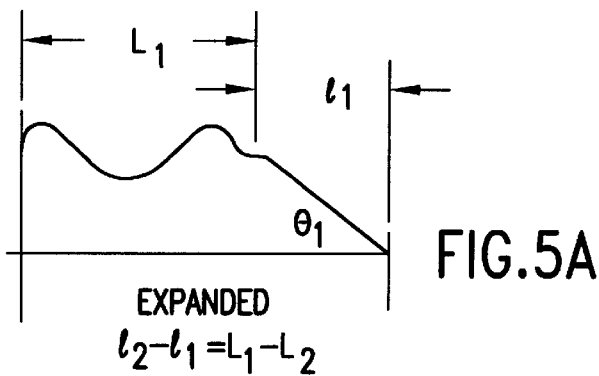
FIG. 5A illustrates the longitudinal component of a strut and its connecting member of the stent of FIGS. 4A and 4B when the stent is in its expanded state.
Figure 5B:
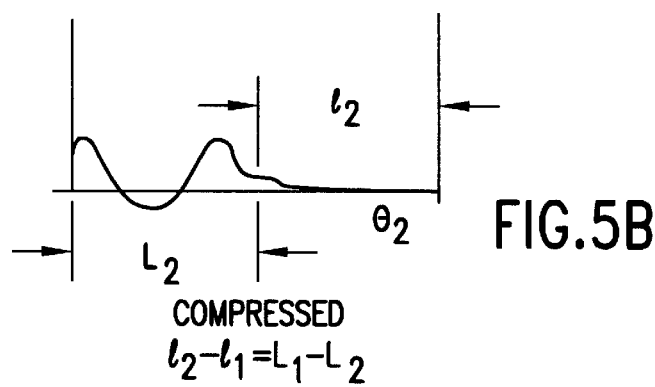
FIG. 5B illustrates the longitudinal component of a strut and its connecting member of the stent of FIGS. 4A and 4B when the stent is in its compressed state.

The connecting members 48 have a configuration that includes a plurality or pattern of alternating segments. A non-limiting first preferred embodiment of the connecting member 48 is illustrated in FIGS. 4A and 4B. Each connecting member 48 extends longitudinally along a longitudinal extension 52 from an apex 46, then slopes upwardly along a curved segment 54 to a top curved apex 56, at which point the connecting member 48 slopes downwardly along a curved segment 58 to a bottom curved apex 60. The connecting member 48 then slopes upwardly along a curved segment 62 to another top curved apex 64. From the top curved apex 64, the connecting member 48 slopes downwardly along a curved segment 66 to a longitudinal extension 68 of the opposing apex 46. Thus, the connecting member 48 has a plurality of alternating curved segments that are defined by the alternating top and bottom apices 56, 60 and 64.

The connecting members 48 are provided to perform two functions. First, the connecting members 48 connect pairs of apices 46. Second, the connecting members 48 function to compensate for the foreshortening experienced by the longitudinal component of each strut 42 and 44, thereby maintaining the stent 40 at substantially the same length at all times. This is accomplished by providing the connecting member 48 with a natural bias and a springy nature, which together with its alternating segments, combine to shorten its length when compressed. When allowed to expand, the connecting member 48 is biased to return to its natural or original position, which lengthens the connecting member 48 to compensate for the foreshortening experienced by the longitudinal component of each strut 42 and 44.

Figure 6A:
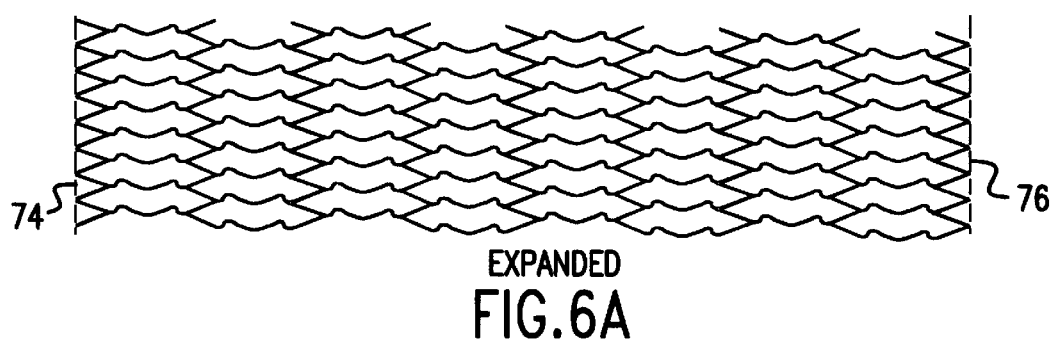
FIG. 6A is a side elevational view of the stent of FIG. 3 in its expanded state.
Figure 6B:
FIG. 6B is a side elevational view of the stent of FIG. 6A in its compressed state.

This effect is illustrated in FIGS. 4A, 4B, 5A and 5B. When the stent 40 is in its compressed state, the connecting member 48 has a length of $L_2$, which is less than the length $L_1$ when the connecting member 48 is in its expanded state. When the connecting member 48 is in the compressed state, its alternating curves have a higher amplitude and a smaller wavelength than when it is in the expanded state (compare FIGS. 4A and 4B). Thus, the difference between $L_2$ and $L_1$ compensates for the difference between $l_1$ and $l_2$ of the struts 42, 44 at both ends of the connecting member 48. The lines 70 and 72 in FIGS. 4A and 4B also show that the relevant portion of the stent 40 does not experience any foreshortening, and the lines 74 and 76 in FIGS. 6A and 6B show that the entire stent 40 maintains a consistent length through all its states.

Although the connecting members 48 have been described in FIGS. 4A, 4B, 5A and 5B as assuming a particular configuration, it will be appreciated by those skilled in the art that the connecting members 48 can assume other configurations without departing from the spirit and scope of the present invention. For example, the connecting members 48 can be provided in any curved, partially curved, or other configuration as long as they function to compensate for the foreshortening experienced by the longitudinal component of each strut 42 and 44.

Figure 7:
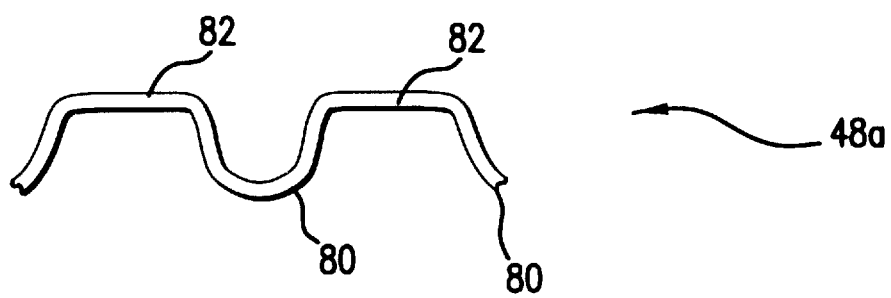
FIGS. 7 and 8 illustrate alternative embodiments of the connecting member according to the present invention.
Figure 8:
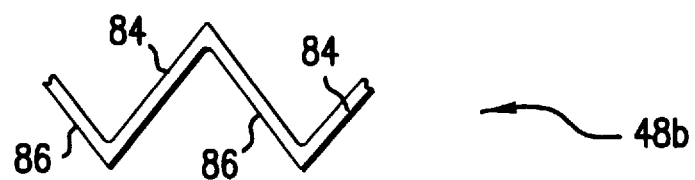

FIG. 7 illustrates a non-limiting second preferred embodiment of the connecting member, in which the connecting member 48a has alternating curved segments 80 and straight segments 82. When the connecting member 48a is compressed, its curved segments 80 also have a higher amplitude and a smaller wavelength than when it is in its expanded state. FIG. 8 illustrates a non-limiting second preferred embodiment, in which the connecting member 48b has alternating straight segments 84 and 86 that are angled with respect to each other.

When the stent 40 is in its fully expanded state, it preferably has an outer diameter that is slightly larger than the inner diameter of the region of the body vessel at which it is to be deployed. This allows the stent 40 to be securely anchored at the desired location and prevents the stent 40 from migrating away from the deployed location.

Figure 9:
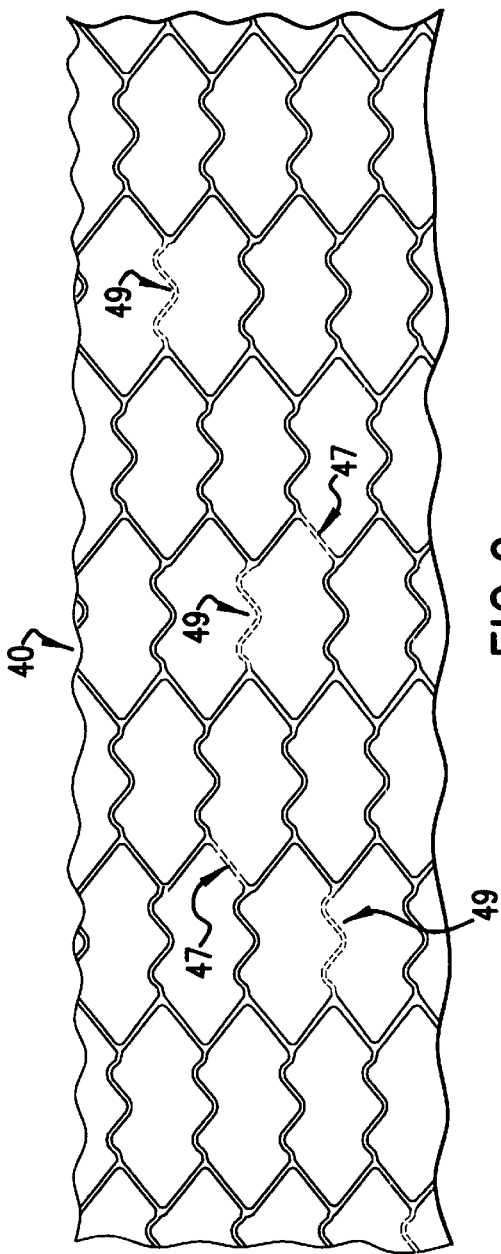
FIG. 9 is a side elevational view of a portion of the stent of FIG. 3 illustrating a modification thereto.

The stent 40 can be provided with varying flexibility or rigidity at different portions or segments along its length to facilitate deployment in body vessels that require such varying flexibility or rigidity. The varying flexibility or rigidity can be accomplished by omitting connecting members 48 and struts 42, 44, or by not connecting one or more struts 32, 44 and/or connecting members 48, thereby creating "gaps" at one or more locations along the stent 40. These locations can be anywhere along the length and/or the circumference of the stent 40. In addition, varying degrees of flexibility in the stent 40 can be accomplished by varying the patterns of these gaps. A non-limiting example would be to provide a substantially spiral pattern of omitted struts 42, 44 and/or connecting members 48, such as illustrated in FIG. 9. The omitted struts 42, 44 and connecting members 48 are illustrated in FIG. 9 in phantom (i.e., the dotted lines) by the numerals 47 (for the struts 42, 44) and 49 (for the connecting members). For example, the omitted struts 47 assume a relatively spiral pattern along the length of the stent 40 from the top left corner of FIG. 9 to the bottom right corner of FIG. 9, and can extend around the circumference of the stent 40. Similarly, the omitted connecting members 49 assume a relatively spiral pattern along the length of the stent 40 from the bottom left corner of FIG. 9 to the top right corner of FIG. 9, and can extend around the circumference of the stent 40.

Other non-limiting alternatives include providing such gaps 49 at one or both ends of the stent 40 only, or at a central portion of the stent 40. Further non-limiting alternatives would be to increase the number of these gaps 47, 49 from one or both ends of the stent 40 towards the center of the stent 40, or to increase the number of these gaps 47, 49 from the center of the stent 40 towards one or both ends of the stent 40. It is also possible to omit only a portion of certain connecting members 48 and not the entire ones of these connecting members 48. A portion of the stent 40 having a larger number of gaps 47, 49 would have greater flexibility or reduced rigidity.

As a result of the omitted struts 47, it is possible that some of the annular elements that are made up of the alternating struts 42, 44 may be closed or constitute completely connected annular elements, while some of these annular elements will be open annular elements.

Figure 10:
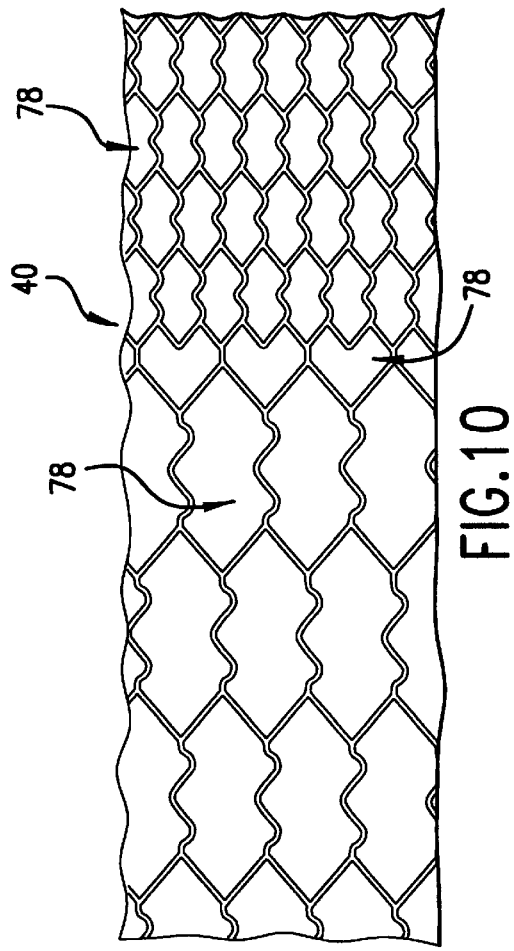
FIG. 10 is a side elevational view of a portion of the stent of FIG. 3 illustrating another modification thereto.

The varying flexibility or rigidity can also be accomplished by providing a structural configuration where the size of the open areas or apertures 78 (for example, see FIGS. 4A and 10) defined between the struts 42, 44 and the connecting members 48 is varied at different portions or segments of the stent 40, along the length and/or circumference of the stent 40. In a non-limiting embodiment, all the apertures 78 in one segment of the stent 40 have substantially the same first size, and all the apertures 78 in another segment of the stent 40 have substantially the same second size, the first and second sizes being different. Additional segments, each having apertures 78 with substantially the same size as the other apertures 78 in that segment but having a different size as the apertures 78 in other segments, can also be provided.

Varying the size of apertures 78 can be accomplished by varying the lengths of the struts 42, 44 and the connecting members 48. For example, a smaller aperture 78 can be provided by shortening the lengths of the struts 42, 44 and the connecting members 48 that define the particular open area 78. Portions of the stent 40 with smaller apertures 78 are more rigid and less flexible than portions of the stent 40 with larger apertures 78. This allows the stent 40 to be deployed in body vessels that require a stent to be more rigid at one end, and to be increasingly flexible from the rigid end. Examples of such body vessels include the renal and iliac arteries discussed above.

Varying the sizes of the apertures 78 also serves other important purposes. For example, providing smaller apertures 78 at the opposing ends of the stent 40 provides increased or closer coverage of the vessel wall, thereby improving support of the diseased vessel wall and preventing fragments of the plaque from being dislodged as embolic debris. The dislodgement of debris can be dangerous in certain vessels, such as the carotid arteries, where dislodged debris can be carried to the brain, possibly resulting in a stroke. As another example, providing larger apertures 78 at central portions of the stent 40 provides wider open areas that may be important in preventing the obstruction of side branches of other body vessels. These wider open areas also allow the passage of guidewires, catheters, stents, grafts, and other deployment devices through the body of the stent 40 into these side branches.

The stent 40 can also be provided in a manner in which it assumes a constant diameter in its compressed state, but in which different portions of the stent 40 can assume different diameters when in their fully expanded states. Providing an expandable stent 40 with the capability of assuming different diameters at different portions is important where the stent 40 is used in certain body vessels or branches of body vessels where the lumen diameters may vary. Examples of such body vessels and branches include the carotid and iliac arteries discussed above, and the esophagus.

Figure 11A:
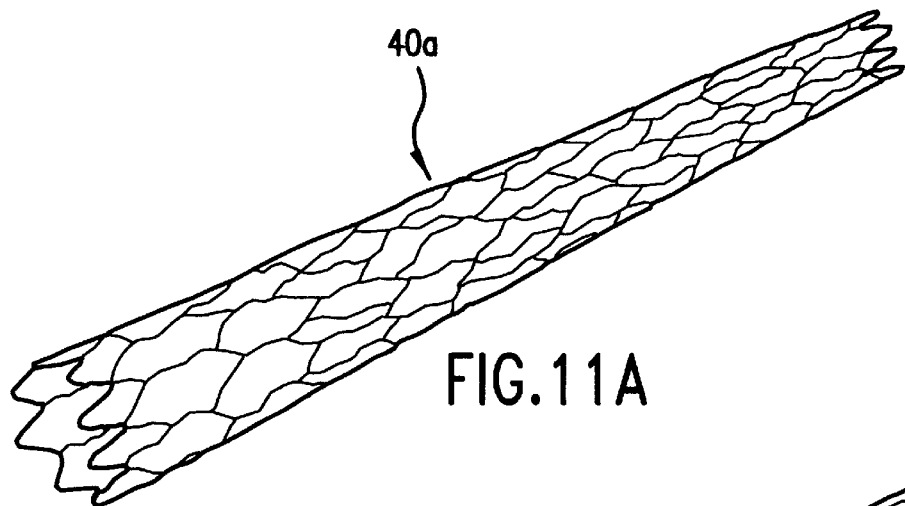
FIGS. 11A–11C illustrate modifications to the stent of FIG. 3.
Figure 11B:
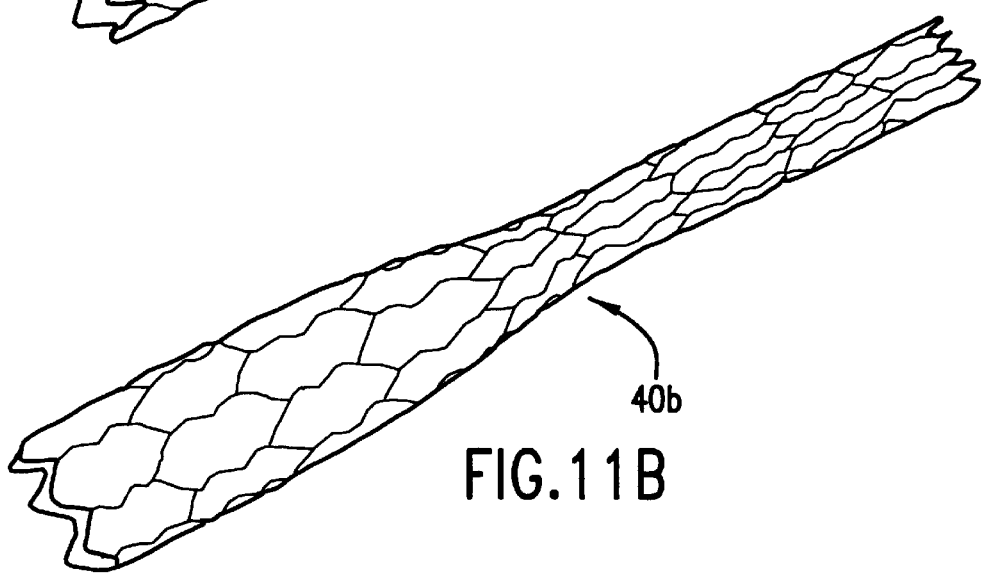
Figure 11C:
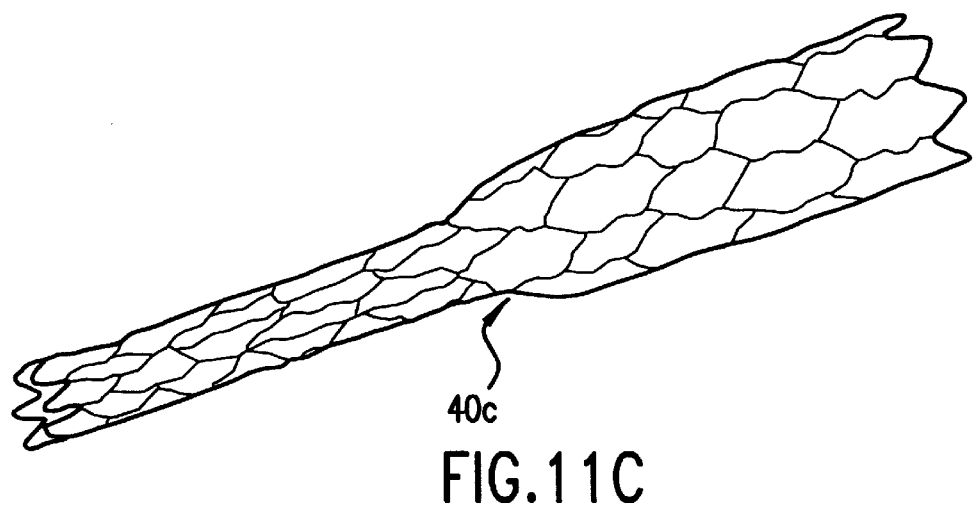

The varying stent diameter can be provided in a number of ways. A first non-limiting alternative is to provide a gradually tapered configuration of the stent 40a, as shown in FIG. 11A. A tapered configuration is best-suited for use in body vessels which experience a gradual narrowing. A second non-limiting alternative is to provide an abrupt transition, such as a stepped configuration, between two stent segments each having a relatively consistent, but different, diameter. The step can be for a step-up 40c, as shown in FIG. 11C, or for a step-down 40b, as shown in FIG. 11B. In addition, a stent 40 can be provided with several changes in diameter along its length to match specific anatomical requirements.

The tapering or transitioning of the stent configuration can be accomplished by pre-shaping, and can be enhanced by variations in (1) the thickness of the stent material, (2) the size of apertures 78, and (3) the gaps 47, 49.

In addition to the above, it will be appreciated by those skilled in the art that varying flexibility and rigidity can also be accomplished by varying the width or thickness of the stent material at certain locations along the length and/or circumference of the stent 40.

A number of materials can be used for both the stent 40 and its struts 42, 44 and connecting members 48, depending on its method of deployment. If used as a self-expanding stent, the stent 40 (including its struts 42, 44 and connecting members 48) is preferably made of a shape memory superelastic metal alloy such as Nitinol, which has the unusual property of "mechanical" memory and trainability. This alloy can be formed into a first predetermined shape above a transition temperature range. The alloy may be plastically deformed into a second shape below the transition temperature range, but the alloy will completely recover to its original (first predetermined) shape when raised back above the transition temperature range. The Nitinol preferably has a composition of about 50% nickel and about 50% titanium. The properties of shape memory alloys such as Nitinol and their use in stents have been well-documented in the literature, and reference can be made to the article by T. W. Duerig, A. R. Pelton and D. Stockel entitled "The Use of Superelasticity in Medicine", a copy of which is attached hereto and specifically incorporated into this specification by specific reference thereto as though fully set forth herein.

Alternatively, the stent 40 (including its struts 42, 44 and connecting members 48) can be made of stainless steel, tantalum, titanium, elgiloy, gold, platinum, or any other metal or alloy, or polymers or composites, having sufficient biocompatibility, rigidity, flexibility, radial strength, radiopacity and antithrombogenicity.

Although the connecting members 48 have been described above as having the same material as the struts 42, 44, it is possible to provide the connecting members 48 with a different material without departing from the spirit and scope of the present invention. Such a material should be springy in nature and should allow the connecting members 48 to be compressed and expanded in the longitudinal direction to compensate for the foreshortening experienced by the struts 42 and 44. Non-limiting examples of such materials can include any of the materials described above for the stent 40.

2. Methods of Manufacture

The stent 40 can be made from one of a number of methods, depending on the material of the stent 40 and the desired nature of deployment.

In a non-limiting first preferred method, the stent 40 is fabricated from a solid Nitinol tube with dimensions that are identical to the stent 40 when it is in the fully compressed state. The pattern of the stent 40 (i.e., its struts 42, 44 and connecting members 48) is programmed into a computer-guided laser cutter or lathe which cuts out the segments between the struts 42, 44 and the connecting members 48 in a manner which closely controls the outside diameter and wall thickness of the stent 40.

After the cutting step, the stent 40 is progressively expanded until it reaches its fully expanded state. The expansion can be performed by an internal expansion fixture, although other expansion apparatus and methods can be used without departing from the spirit and scope of the present invention. The overall length of the stent 40 must be consistently maintained throughout the expansion of the stent 40 from its fully compressed to its fully expanded states.

Once the stent 40 has been expanded to its fully expanded state, it is heat-treated to "set" the shape memory of the Nitinol material to the fully expanded dimensions. The stent 40 is then cleaned and electro-polished.

The next step is to compress the stent 40 again into a dimension which allows for delivery into a vessel, either through percutaneous delivery or through minimally invasive surgical procedures. Specifically, the stent 40 must be compressed into a smaller state so that it can be delivered by a delivery device to the desired location of the vessel. Any conventional delivery device could be used, such as but not limited to a tube, catheter, or sheath. This compression is accomplished by cooling the stent 40 to a low temperature, for example, zero degrees Celcius, and while maintaining this temperature, compressing the stent 40 to allow the stent 40 to be inserted inside the delivery device. Once inserted inside the delivery device, the stent 40 is held by the delivery device in the compressed state at room temperature.

In a non-limiting second preferred method, a balloon-expandable stent 40 can be fabricated by connecting a plurality of wires that have been bent or formed into the desired shapes for the struts 42, 44 and connecting members 48. The connection can be accomplished by welding, tying, bonding, or any other conventional method. Alternatively, wire electro-discharge machining can be used. The wires are capable of experiencing plastic deformation when the stent 40 is compressed, and when the stent 40 is expanded. Upon plastic deformation of the stent 40 to either the compressed or the expanded state, the stent 40 remains in this state until another force is applied to plastically deform the stent 40 again.

While certain methods of manufacture have been described above, it will be appreciated by those skilled in the art that other methods of manufacture can be utilized without departing from the spirit and scope of the present invention.

3. Deployment Methods

The stent 40 can be deployed by a number of delivery systems and delivery methods. These delivery systems and methods will vary depending on whether the stent 40 is expanded by self-expansion, radial expansion forces, or radio frequency.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A stent comprising:
   a plurality of annular elements, each annular element having a compressed state and an expanded state, wherein each annular element has a longitudinal dimension which is smaller in the radially expanded state than in the compressed state; and
   connecting members connecting adjacent annular elements;
   wherein the annular elements and connecting members are made of Nitinol, with each connecting member preset with an elasticity which causes the connecting member to elongate longitudinally when the annular elements are in their expanded state to compensate for the smaller longitudinal dimension of the annular elements in the expanded state.

2. The stent of claim 1, wherein each annular element comprises a plurality of alternating struts and apices connected to each other to form a substantially annular configuration.

3. The stent of claim 2, wherein the connecting members are connected to the apices of the adjacent annular members.

4. The stent of claim 2, wherein the plurality of struts comprises left and right struts, with each pair of left and right struts connected to each other at an apex.

5. The stent of claim 2, wherein each strut has a longitudinal dimensional which is smaller when the annular elements are in the expanded state than in the compressed state.

6. The stent of claim 2, wherein each strut has a longitudinal dimensional which is larger when the annular elements are in the compressed state than in the expanded state.

7. The stent of claim 2, wherein at least one of the annular elements is closed such that the plurality of alternating struts and apices are connected to each other to form a closed annular element.

8. The stent of claim 7, wherein at least one of the annular elements are open such that the plurality of alternating struts and apices are not connected at at least one location.

9. The stent of claim 1, wherein at least of connecting member has a plurality of alternating segments.

10. The stent of claim 9, wherein the connecting member has a plurality of alternating curved segments defining alternating top and bottom curved apices.

11. The stent of claim 10, wherein each of the plurality of alternating curved segments has an amplitude and a wavelength, and wherein the plurality of alternating curved segments have a smaller amplitude and a greater wavelength when the annular elements are in the expanded state than when the annular elements are in the compressed state.

12. The stent of claim 9, wherein the at least one connecting member has a plurality of alternating curved and straight segments.

13. The stent of claim 9, wherein the at least one connecting member has a plurality of alternating and angled straight segments.

14. The stent of claim 1, wherein each connecting member has a larger longitudinal dimension when each annular element is in the expanded state than in the compressed state to compensate for the smaller longitudinal dimension of the annular element in the expanded state.

15. The stent of claim 1, wherein each connecting member has a smaller longitudinal dimension when each annular element is in the compressed state than in the expanded state to compensate for the larger longitudinal dimension of the annular element in the compressed state.

16. The stent of claim 1, wherein the stent has a plurality of segments along its length, each segment assuming a different diameter when the annular elements are in their expanded state.

17. The stent of claim 16, wherein the stent has a tapered configuration in which the diameter of the stent gradually changes from one segment to another segment.

18. The stent of claim 16, wherein the stent has a stepped configuration in which the diameter of the stent transitions abruptly from one segment to another segment.

19. The stent of claim 1, further in combination with a biocompatible graft covering.

20. The stent of claim 1, wherein the annular elements and connecting members define an alternating longitudinal pattern of annular elements and connecting members.

21. A stent having a first segment and a second segment, with each segment having a diameter and comprising:
   a plurality of annular elements, each annular element having a compressed state and an expanded state;
   at least one connecting member connecting adjacent annular elements;
   a plurality of apertures defined by adjacent annular elements and connecting members, each aperture having a size and a geometric configuration;
   with the first and second segments having substantially the same diameter in the compressed state; and
   wherein the apertures of the first and second segments have different sizes but substantially the same geometric configuration when the first and second segments are in the expanded state.

22. The stent of claim 21, wherein each annular element comprises a plurality of alternating struts and apices connected to each other to form a substantially annular configuration, and wherein the connecting members are connected to the apices of the adjacent annular members, with the apertures defined by the adjacent struts and connecting members.

23. The stent of claim 21, wherein each segment of the stent assumes a different diameter when the annular elements are in their expanded state.

24. The stent of claim 23, wherein the stent has a tapered configuration in which the diameter of the stent gradually changes from one segment to another segment.

25. The stent of claim 23, wherein the stent has a stepped configuration in which the diameter of the stent transitions abruptly from one segment to another segment.

26. The stent of claim 21, wherein the at least one connecting member has a plurality of alternating segments.

27. The stent of claim 26, wherein the at least one connecting member has a plurality of alternating curved segments defining alternating top and bottom curved apices.

28. The stent of claim 27, wherein each of the plurality of alternating curved segments has an amplitude and a wavelength, and wherein the plurality of alternating curved segments have a smaller amplitude and a greater wavelength when the annular elements are in the expanded state than when the annular elements are in the compressed state.

29. The stent of claim 26, wherein the at least one connecting member has a plurality of alternating curved and straight segments.

30. The stent of claim 26, wherein the at least one connecting member has a plurality of alternating and angled straight segments.

31. The stent of claim 21, wherein the stent is made from Nitinol.

32. The stent of claim 21, wherein each annular element comprises a plurality of alternating struts and apices connected to each other to form a substantially annular configuration, with at least one of the annular elements provided in an open configuration such that the plurality of alternating struts and apices are not connected at at least one location.

33. A stent having a plurality of segments and comprising:
   a plurality of annular elements, each annular element having a compressed state and an expanded state;
   a plurality of connecting members connecting adjacent annular elements; and
   a plurality of gaps formed by omitting at least one of the connecting members between adjacent annular elements so as to provide two of the plurality of segments of the stent with different degrees of flexibility.

34. The stent of claim 33, wherein a plurality of connecting members are omitted, with the omitted connecting members forming a spiral pattern.

35. A stent having a plurality of segments and comprising:
   a plurality of annular elements, each annular element having a compressed state and an expanded state;
   a plurality of connecting members connecting adjacent annular elements; and
   wherein each annular element comprises a plurality of alternating struts and apices connected to each other to form a substantially annular configuration, and wherein the connecting members are connected to the apices of the adjacent annular elements;
   and wherein a plurality of gaps are formed by omitting at least one of the struts so as to provide two of the plurality of segments of the stent with different degrees of flexibility.

36. The stent of claim 35, wherein the plurality of gaps is further formed by omitting at least one of the connecting members between adjacent annular elements.

37. The stent of claim 35, wherein a plurality of struts are omitted, with the omitted struts forming a spiral pattern.

38. A stent comprising:
   a plurality of annular elements, each annular element having a compressed state and an expanded state, and each annular element including a plurality of alternating struts and apices connected to each other to form a substantially annular configuration; and
   at least one connecting member connecting adjacent annular elements;
   wherein at least one of the annular elements is closed such that the plurality of alternating struts and apices are connected to each other to form a closed annular element, and wherein at least one of the annular elements are open such that the plurality of alternating struts and apices are not connected at at least one location.

39. The stent of claim 38, wherein the at least one connecting member is connected to the apices of the adjacent annular members.

40. The stent of claim 38, wherein the plurality of struts comprises left and right struts, with each pair of left and right struts connected to each other at an apex.

41. The stent of claim 38, wherein each strut has a longitudinal dimensional which is smaller when the annular elements are in the expanded state than in the compressed state.

42. The stent of claim 38, wherein each strut has a longitudinal dimensional which is larger when the annular elements are in the compressed state than in the expanded state.

43. The stent of claim 38, wherein the at least one connecting member has a plurality of alternating segments.

44. The stent of claim 43, wherein the at least one connecting member has a plurality of alternating curved segments defining alternating top and bottom curved apices.

45. The stent of claim 44, wherein the plurality of alternating curved segments have a higher amplitude and a smaller wavelength when the annular elements are in the expanded state than when the annular elements are in the compressed state.

46. The stent of claim 43, wherein the at least one connecting member has a plurality of alternating curved and straight segments.

47. The stent of claim 43, wherein the at least one connecting member has a plurality of alternating and angled straight segments.

48. The stent of claim 38, wherein the at least one connecting member is preset with an elasticity which causes the connecting member to elongate longitudinally when the annular elements are in their expanded state to compensate for the smaller longitudinal dimension of the annular elements in the expanded state.

49. The stent of claim 48, wherein the stent is made from Nitinol.

50. The stent of claim 38, wherein the annular elements and the at least one connecting member define an alternating longitudinal pattern of annular elements and connecting members.

51. The stent of claim 38, wherein the stent has a plurality of segments along its length, each segment assuming a different diameter when the annular elements are in their expanded state.

52. The stent of claim 51, wherein the stent has a tapered configuration in which the diameter of the stent gradually changes from one segment to another segment.

53. The stent of claim 51, wherein the stent has a stepped configuration in which the diameter of the stent transitions abruptly from one segment to another segment.

54. The stent of claim 38, further in combination with a biocompatible graft covering.

* * * * *